United States Patent [19]
Legendre et al.

[11] Patent Number: 5,614,672
[45] Date of Patent: Mar. 25, 1997

[54] APPARATUS FOR MEASURING THE LIQUID CONTENTS OF A TANK

[76] Inventors: W. J. Legendre; Christopher Dore, both of P.O. Box 84158, Baton Rouge, La. 70884-4158

[21] Appl. No.: 589,972

[22] Filed: Jan. 23, 1996

[51] Int. Cl.⁶ .................................................. G01N 9/10
[52] U.S. Cl. ............................................................ 73/437
[58] Field of Search ............................. 73/149, 309, 433, 73/437

[56] References Cited

U.S. PATENT DOCUMENTS

| | | | |
|---|---|---|---|
| 2,342,696 | 2/1944 | Rover | 73/309 |
| 2,416,570 | 2/1947 | Coleman | 73/309 |
| 4,945,756 | 8/1990 | Lewis et al. | 73/309 |
| 5,132,923 | 7/1992 | Crawford et al. | 73/309 |
| 5,157,968 | 10/1992 | Zfira . | |

*Primary Examiner*—Robert Raevis
*Attorney, Agent, or Firm*—Robert N. Montgomery

[57] ABSTRACT

Apparatus for measuring weight, level and or volume of a volatile liquid in a sealed container, comprising: a housing, capable of sustaining high pressure; a load cell, located within the pressure housing, mounted on an external pipe flange at the top of a sealed container having known cross section and containing a liquid of a known specific gravity; a displacer weight of known weight and length passing through the pipe flange opening and suspended above the bottom of the container. The apparatus, operating on the inferential method of determining liquid quantity by weight in a sealed vessel, works on the principle that when there is no liquid in the tank, the load-cell and its meter system sense the maximum weight of a displacer cylinder which is the null or "Zero" point for measurement. The buoyancy of the displacer weight in the liquid then reflects the volume in the container via a meter/computer display.

15 Claims, 3 Drawing Sheets

APPARATUS FOR MEASURING THE LIQUID CONTENTS OF A TANK

BACKGROUND OF THE INVENTION

1. Field of the Invention

The present invention relates to an apparatus for measuring the amount of liquid in a tank and, more particularly, to an apparatus for measuring the weight, level and/or volume of a liquid in a sealed container.

2. General Background

The prior art suggests a number of methods and apparatus for measuring the liquid level in a tank. Some utilize ultrasonics while others use a float system in combination with the magnetostrictive principle. Other apparatus rely on sensor arrays to determine the mass of the liquid in a container then calculating the volume based on the mass, specific gravity of the liquid and adjusting for temperature variations. All such devices and systems have one thing in common, they all have various degrees of error. Each system strives to reduce the error, and in doing so, the systems become more complicated. One such system is disclosed by Zfira in U.S. Pat. No. 5,157,968. Zfira discloses a system for measuring the specific gravity, weight, level and/or volume of a liquid in a container. However, Zfira employs a dual system, one for measuring specific gravity where the liquid may change from time to time and the second for measuring the mass of the liquid thus determining the quantity of liquid in the container. The system requires two load cells, two body weights and two transmitters to send data to a computer monitoring system which, in effect, produces two input signals, thereby, inducing a second error factor. Any system which relies on multiple sensors or inputs compounds its potential for error. The Zfira patent does not disclose a means for operating under pressure. The known systems are usually relatively complicated and are limited as to the types of liquid measured without using multiple sensors. Such systems do not address the need for a simple system having a single input for measuring a known type of material, contained in a vessel, designed for storing a specific volatile liquid. In some such cases, it is essential that the apparatus be capable of operating while under pressure and be calibrated without opening the enclosure or otherwise disturbing the integrity of the vessel.

SUMMARY OF THE PRESENT INVENTION

It is an object of the present invention to provide a simple and efficient apparatus which may be used for measuring the mass, level and/or volume of a volatile liquid under pressure, in a container, regardless of its temperature variation.

Another object of the invention is to provide an apparatus which can monitor the mass of liquid in a sealed tank or vessel in real time, as the level changes, with only one input signal. Still another object of the invention is to provide a load cell apparatus for taking such measurements in a pressure tested housing for mounting to a container's existing pipe flange. According to the present invention, there is provided an apparatus for measuring the mass and/or volume of a liquid of known specific gravity, in a container of known cross sectional area. The apparatus is comprised of; a load cell device at the upper end of the container, mounted in a pressure tested housing, attached to the tank or container's spool flange, in a vertical position; a sealed, hollow, cylindrical free-body having a uniform cylindrical configuration of a known cross sectional area and weight, the free-body extending through the interior of the container, with the upper end of the body supported by the load cell, with the lower end of the free-body clear of the container bottom, the free-body being adaptable in length, depending on the container depth, the free-body referred to herein as a displacer, having a diameter and weight which depends on the container depth, specific gravity of the fluid to be measured, and in some cases, the size of the container flange, the displacer being of sufficient length so that it would normally be only partially submerged by the liquid in the container; and a power supply/signal conditioner located adjacent the load cell for excitation of the load cell and electrically transmitting the signals generated by the load cell as a result of movement by the displacer's buoyancy in the liquid, to a remote computer for interpretation of the tank's mass and/or volume of the liquid in the container.

This method of measurement, known as an inferential method of determining liquid quantity by weight in a sealed vessel, works on the principle that when there is no liquid in the tank, the load-cell and its meter system senses the maximum weight of the displacer which is the null or "Zero" point for measurement. As the known liquid rises, the load cell senses less strain due to the buoyancy of the displacer cylinder at a given specific gravity, depth and pressure. Although the liquid in the container expands with temperature increase, the liquid level on the displacer cylinder will increase and the specific gravity of the fluid will proportionately drop. The load cell will not see any change since the total weight of the liquid in the tank has not changed. Therefore, there is no need for temperature compensation of measured values since the free body or displacer cylinder sees only the weight of the fluid it displaces and not simply the liquid level.

BRIEF DESCRIPTION OF TEE DRAWINGS:

For a further understanding of the nature and objects of the present invention, reference should be had to the following detailed description, when taken in conjunction with the accompanying drawings, in which like parts are given like reference numerals, and wherein.

DESCRIPTION OF TEE PREFERRED EMBODIMENT

Figure 1:
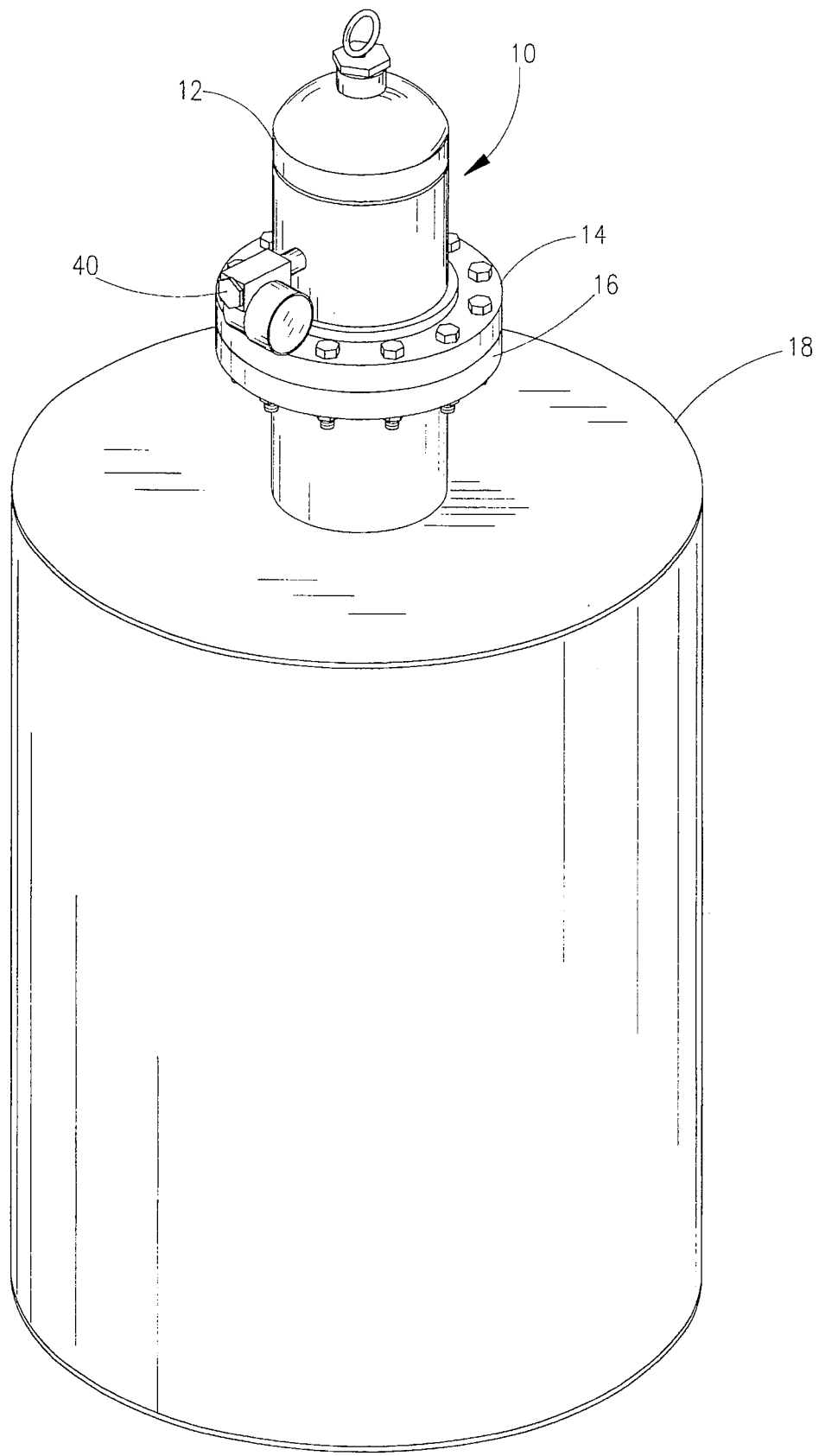
FIG. 1 is an isometric, elevation view of the preferred embodiment as typically installed on a container.
Figure 2:
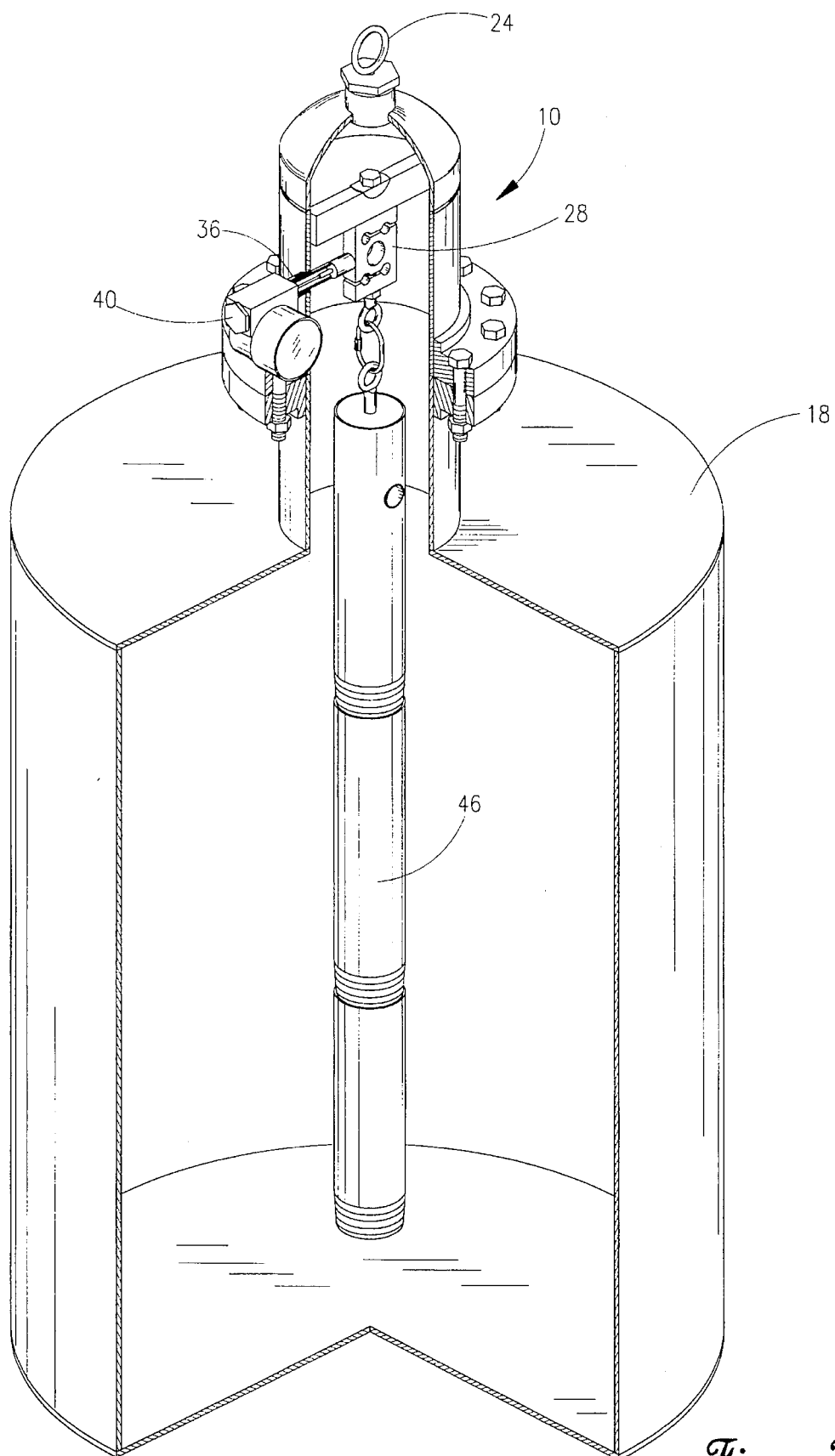
FIG. 2 is a cut-a-way, isometric, elevation view of the preferred embodiment as typically installed on a container.
Figure 3:
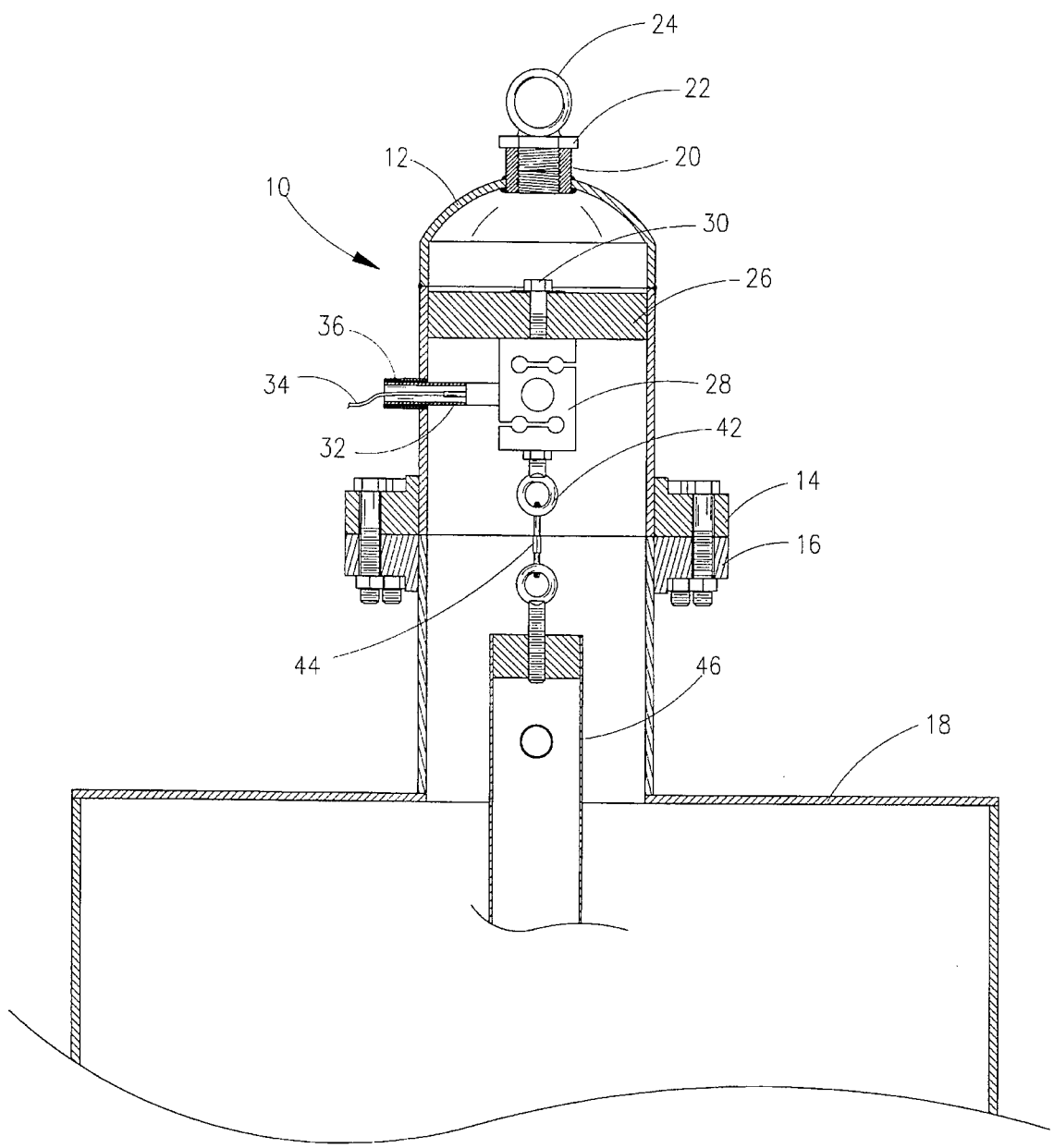
FIG. 3 is an elevation, cross section view of the preferred embodiment as typically installed on a container.

The present invention 10 as first seen in FIG. 1, is comprised of a dome shaped, pressurable housing 12 having a heavy, external flange collar 14 for coupling to a mating flange 16 on a container or vessel 18, as best seen in FIG. 3, with the dome of the housing 12 fitted with a threaded coupling 20 at its peak and externally plugged with a hex-head, pipe plug 22 having a lifting ring 24 secured thereto. The housing 12 further contains a support bar 26 secured internally for supporting a load cell 28. A load cell 28 is attached to the internal support bar 26 via a bolt 30 and is fitted with a pipe nipple 32 secured at one end to the load cell 28 thereby providing a conduit for the load cell cable 34. An externally threaded pipe nipple 36, which penetrates the side wall of the housing 12, is also provided and is seal welded at its open end to the load cell nipple 32. A transmitter/meter 40 having a power supply and a signal conditioning system may be threadably attached directly to the penetration nipple 36 for receiving and connection of, the load cell power and signal cable 34. Regardless of its location the power supply/signal conditioner provides excitation voltage to the load cell and receives signals from the load cell for transmission to a remote computer. An eyelet 42 is provided at the lower end of the load cell 28 for pivotal attachment 44 of a hollow, sealed, displacer 46 which is of known weight and length. The cylinder body or displacer 46 is capable of length adjustment as best seen in FIG. 2.

Because many varying and different embodiments may be made within the scope of the inventive concept herein taught and because many modifications may be made in the embodiments herein detailed in accordance with the descriptive requirement of the law, it is to be understood that the details herein are to be interpreted as illustrative and not intended to limit the invention.

What is claimed is:

1. An apparatus for measuring weight, level and/or volume of a liquid of known, specific gravity in a container of known cross-sectional area without the need to compensate for temperature or disturbing the integrity of a pressurized tank, comprising:

a) a housing, having a domed portion, a vertical side portion and a flange portion, capable of sustaining high pressure, mountable to a compatible flanged connection port at an upper end of a pressurized liquid container, said housing further comprising a first pipe nipple exiting said vertical side portion;

b) a load cell mounted at one end to a support bar, located within said housing;

c) a buoyant, extendable, cylindrical body of known cross section, weight and length, suspended from said load cell opposite said mounted end; and d) a second pipe nipple connected to said first pipe nipple, extending telescopically through said first pipe nipple, attached to said load cell; and e) a power supply/signal cable passing through said second pipe nipple connected electrically to said load cell.

2. The apparatus, according to claim 1, wherein said load cell is mounted vertically to said support bar and wherein said power supply/signal cable and said second pipe nipple are attached perpendicularly to said load cell relative to an axis passing through the mounting of said load cell to said support bar and the point of suspension of said cylindrical body.

3. The apparatus, according to claim 2, wherein said first and second pipe nipples are seal welded, thereby forming a pressure seal around said power supply/signal cable.

4. The apparatus, according to claim 3, wherein said power/supply signal cable supplies excitation voltage to the load cell receives Signals from the load cell, thereby, converting mechanical force into electrical signals, for display on a local display meter, and/or transmitted electrically to remote computer.

5. The apparatus according to claim 4, wherein said local display meter is removable and calibrateable without disturbing the integrity of the container under pressure.

6. The apparatus, according to claim 3, wherein said cylindrical body is hollow, of uniform configuration and extendable by adding threaded sections.

7. The apparatus, according to claim 6, wherein said cylindrical body is connected to said load cell via pivotal attachments thereby suspending said cylindrical body in said liquid container via said flanged connection port.

8. The apparatus, according to claim 7, wherein said cylindrical body is held in suspension by said load cell with its lower end slightly above said liquid container bottom and is buoyantly suspended by a liquid of a known specific gravity.

9. The apparatus according to claim 8, further including computing means for receiving the output signal from said signal cable for computing and displaying weight, level and/or volume of the liquid of known specific gravity of the liquid in the container, at a remote location.

10. An apparatus for measuring mass of a liquid of specific gravity, in a container, under pressure, in a tank of known cross-sectional area, without the need to compensate for temperature, comprising:

a) a housing, having a domed portion, a vertical side portion and a flange portion, capable of sustaining high pressure, mountable to a compatible flanged connection port at an upper end of a pressurized liquid container, said housing further comprising a first pipe nipple exiting said vertical side portion;

b) a load cell mounted at one end to a support bar located within said housing;

b) a hollow cylindrical body of known cross section, weight and length, suspended from said load cell and passing through said flanged connection and interior of the container to a point near said container bottom;

c) an explosion proof housing containing a transmitter/meter attached to said domed housing said transmitter/meter being isolated atmospherically from the interior of said domed housing; and d) an electrical cable connecting said load cell to said transmitter/meter.

11. The apparatus, according to claim 10, wherein said cylindrical body is of uniform configuration.

12. The apparatus, according to claim 11, wherein said cylindrical body is a hollow, sealable, cylindrical body, extendible by adding sections of various lengths.

13. The apparatus, according to claim 12, wherein the transmitter/meter further provides excitation voltage to the load cell and receives signals from the load cell having first converted mechanical force into electrical signals for display said weight, level and/or volume based on mass to said transmitter/meter and/or transmission to a remote computer.

14. The apparatus, according to claim 13, wherein said transmitter/meter is capable of being removed or calibrated electrically without disturbing the integrity of container while under pressure.

15. The apparatus, according to claim 14, wherein said remote computer further includes computing means for receiving the output signal from said transmitter/medium meter and computing and displaying weight, level and/or volume of liquids of known specific gravity in said container without compensating for temperature differential in said pressurized container.

* * * * *